United States Patent
Genkin et al.

(10) Patent No.: US 9,770,492 B2
(45) Date of Patent: Sep. 26, 2017

(54) METHOD FOR TREATING SYSTEMIC DNA MUTATION DISEASE

(71) Applicant: CLS Therapeutics Limited, Guernsey, Channel Islands (GB)

(72) Inventors: Dmitry Dmitrievich Genkin, Saint-Petersburg (RU); Georgy Viktorovich Tets, Saint-Petersburg (RU); Viktor Veniaminovich Tets, Saint-Petersburg (RU)

(73) Assignee: CLS Therapeutics Limited, Guernsey (GB)

( * ) Notice: Subject to any disclaimer, the term of this patent is extended or adjusted under 35 U.S.C. 154(b) by 0 days.

(21) Appl. No.: 15/157,910

(22) Filed: May 18, 2016

(65) Prior Publication Data

US 2016/0303204 A1    Oct. 20, 2016

Related U.S. Application Data

(60) Division of application No. 14/309,363, filed on Jun. 19, 2014, now Pat. No. 9,463,223, which is a continuation of application No. 13/772,499, filed on Feb. 21, 2013, now Pat. No. 8,796,004, which is a continuation of application No. 12/835,029, filed on Jul. 13, 2010, now Pat. No. 8,388,951, which is a continuation-in-part of application No. 10/564,609, filed as application No. PCT/RU2004/000260 on Jul. 1, 2004, now abandoned.

(30) Foreign Application Priority Data

Jul. 14, 2003    (WO) ................ PCT/RU2003/000304
Mar. 12, 2004    (RU) ................................ 2004108057

(51) Int. Cl.
| | |
|---|---|
| *A61K 38/46* | (2006.01) |
| *C12Q 1/68* | (2006.01) |
| *C12N 9/16* | (2006.01) |
| *C12N 9/22* | (2006.01) |

(52) U.S. Cl.
CPC .......... *A61K 38/465* (2013.01); *C12Q 1/6883* (2013.01); *C12Y 301/00* (2013.01); *C12Y 301/21001* (2013.01); *C12Q 2600/156* (2013.01)

(58) Field of Classification Search
CPC ................ A61K 38/465; C12Q 1/6883; C12Q 2600/156; C12Y 301/21001
See application file for complete search history.

(56) References Cited

U.S. PATENT DOCUMENTS

| | | |
|---|---|---|
| 4,485,095 A | 11/1984 | Fujisaki et al. |
| 5,484,589 A | 1/1996 | Salganik et al. |
| 5,656,589 A | 8/1997 | Stossel et al. |
| 5,830,744 A | 11/1998 | Rosen et al. |
| 5,855,920 A | 1/1999 | Chein |
| 5,889,153 A | 3/1999 | Suzuki et al. |
| 5,952,170 A | 9/1999 | Stroun et al. |
| 6,033,846 A | 3/2000 | Fourine |
| 6,156,504 A | 12/2000 | Gocke et al. |
| 6,391,607 B1 | 5/2002 | Lazarus et al. |
| 6,428,785 B1 | 8/2002 | Gokeen |
| 6,455,250 B1 | 9/2002 | Aguilera et al. |
| 6,465,177 B1 | 10/2002 | Hoon |
| 6,521,409 B1 | 2/2003 | Gocke et al. |
| 7,402,724 B2 | 7/2008 | Conover |
| 7,612,032 B2 | 11/2009 | Genkin et al. |
| 2003/0044403 A1 | 3/2003 | Shak |
| 2004/0001817 A1 | 1/2004 | Giampapa |
| 2004/0157239 A1 | 8/2004 | Tanuma et al. |
| 2006/0228347 A1 | 10/2006 | Sunaga et al. |
| 2006/0233780 A1 | 10/2006 | Genkin et al. |
| 2008/0004561 A1 | 1/2008 | Genkin et al. |
| 2009/0047272 A1 | 2/2009 | Appelbaum et al. |
| 2009/0053200 A1 | 2/2009 | Genkin et al. |
| 2010/0061971 A1 | 3/2010 | Genkin et al. |
| 2010/0150903 A1 | 6/2010 | Genkin et al. |
| 2011/0033438 A1 | 2/2011 | Bartoov et al. |
| 2011/0070201 A1 | 3/2011 | Shaaltiel et al. |
| 2011/0189156 A1 | 8/2011 | Genkin et al. |

FOREIGN PATENT DOCUMENTS

| | | |
|---|---|---|
| CA | 2394856 A1 | 6/2001 |
| CA | 2184582 C | 12/2001 |
| DE | 4024530 A1 | 2/1992 |
| DE | 10221194 A1 | 12/2003 |
| EP | 0325191 A2 | 7/1989 |
| EP | 1431762 A1 | 6/2004 |
| EP | 1655036 A1 | 5/2006 |

(Continued)

OTHER PUBLICATIONS

Anker, P. et al., Tumor-related alterations in circulating DNA, potential for diagnosis, prognosis and detection of minimal residual disease, Leukemia, 15, 289-91, 2001.
Ashton, G., Growing pains for biopharmaceuticals, Nature Biotech, vol. 19, pp. 307-311, 2001.
Aung et al., Current status and future potential of somatic mutation testing from circulating free DNA in patients with solid tumours, HUGO J, vol. 4, pp. 11-21, 2010.
Botto, N., al., Elevated levels of oxidative DNA damage in patients with coronary artery disease, Coronary Artery Disease, vol. 13, pp. 289-274, 2002.
Boyko et at., Cell-free DNA—a marker to predict ischemic brain damage in a rat stroke experimental model, Journal of Neurosurgical Anesthesiology, vol. 23, pp. 222-228, 2011.
Burt et al., Detection of circulating donor deoxyribonucleic acid by microsatellite analysis in a liver transplant recipient. Liver Transpl Surg. (2), pp. 391-394, 1996.

(Continued)

*Primary Examiner* — Delia Ramirez
(74) *Attorney, Agent, or Firm* — Troutman Sanders LLP

(57) ABSTRACT

The invention is directed to treatment of systemic DNA mutation diseases accompanied with development of somatic mosaicism and elevation of blood extracellular DNA. The inventive method comprises introducing a DNASE enzyme into the systemic blood circulation of a patient in doses and regimens which are sufficient to decrease average molecular weight of circulating extracellular blood DNA in the blood of said patient.

5 Claims, 1 Drawing Sheet

(56) References Cited

FOREIGN PATENT DOCUMENTS

| | | |
|---|---|---|
| EP | 1666055 A1 | 6/2006 |
| EP | 1880733 A1 | 1/2008 |
| EP | 2095825 B1 | 6/2011 |
| GB | 984464 A | 2/1965 |
| GB | 1005985 A | 9/1965 |
| JP | 61293927 A | 12/1986 |
| JP | 2006290769 A | 10/2006 |
| NZ | 299257 A | 8/2000 |
| RU | 2099080 C1 | 12/1997 |
| RU | 2001104426 A | 1/2003 |
| RU | 2202109 C1 | 4/2003 |
| RU | 2207876 C1 | 7/2003 |
| RU | 2239404 C1 | 11/2004 |
| RU | 2239442 C1 | 11/2004 |
| RU | 2267329 C2 | 1/2006 |
| RU | 2269356 C2 | 2/2006 |
| RU | 2269357 C2 | 2/2006 |
| RU | 2269359 C2 | 2/2006 |
| RU | 2308968 C2 | 10/2007 |
| WO | 9303709 A1 | 3/1993 |
| WO | 9500170 A1 | 1/1995 |
| WO | 9728266 A1 | 8/1997 |
| WO | 9747751 A1 | 12/1997 |
| WO | 0003709 A1 | 1/2000 |
| WO | 0031238 A1 | 6/2000 |
| WO | 0174905 A1 | 10/2001 |
| WO | 03068254 A1 | 8/2003 |
| WO | 2005004903 A1 | 1/2005 |
| WO | 2005004904 A1 | 1/2005 |
| WO | 2005007187 A1 | 1/2005 |
| WO | 2005115444 A2 | 12/2005 |
| WO | 2006130034 A1 | 12/2006 |
| WO | 2008-047364 A2 | 4/2008 |
| WO | 2008066403 A1 | 6/2008 |
| WO | 2011-073665 A1 | 6/2011 |
| WO | 2012075506 A2 | 6/2012 |
| WO | 2014020564 A1 | 2/2014 |

OTHER PUBLICATIONS

Davis JC et al., Recombinant human Dnase I (rhDNase) in patients with lupus nephritis, Lupus, vol. 8, pp. 68-76, 1999.

Davis, Brian R. et al., Somatic mosaicism in the Wiskott-Aldrich syndrome: Molecular and functional characterization of genotypic revertants, Clinical Immunology, vol. 135, pp. 72-83, 2010.

Dayan, Pharmacological-Toxicological (Expert Report on Recombinant Human Deoxyribonuclease I (rhDNase; PulmozymeTM), Hum. Exp. Toxicol., 13: S2, 1994.

Deitsch, et al., Transformation of malaria parasites by the spontaneous uptake and expression of DNA from human erythrocytes, Nucleic Acids Research, vol. 29, pp. 850-853, 2000.

Deocharan B., et al., Alpha-actinin is a cross-reactive renal target for pathogenic anti-DNA antibodies, J. Immunol., vol. 168, pp. 3072-3078, 2002.

Department of Health and Human Services Food and Drug Administration, Federal Register, Dec. 13, 1985, vol. 50, No. 240.

Dittmar, Manuela et al., A novel mutation in the DNASE1 gene is related with protein instability and decreased enzyme activity in thyroid autoimmunity, Journal of Autoimmunity, vol. 32, pp. 7-13, 2009.

El Hassan NO, et al. Rescue use of Dnase in critical lung atelectasis mucus retention in premature neonates, Pediatrics., vol. 108, pp. 468-470, 2001.

Erickson, Robert P., Somatic gene mutation and human disease other than cancer, Mutation Research, vol. 543, pp. 125-136, 2003.

Erickson, Robert P., Somatic gene mutation and human disease other than cancer: An update, Mutation Research, vol. 705, pp. 96-106, 2010.

Extended European Search Report for European Patent Appl. No. EP12170750 dated Aug. 3, 2012.

Extended European Search Report for European Patent Appl. No. EP12170754 dated Aug. 3, 2012.

Extended European Search Report for European Patent Appl. No. EP12170757 dated Aug. 3, 2012.

Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).

Freshney, R. I., Culture of Animal Cells, A Manual of Basic Technique, Alan R. Liss, Inc., New York, pp. 3-4, 1983.

Funakoshi, A, et al., Clinical Investigation of Serum Deoxyribonuclease: II. Clinical Studies of Serum Deoxyribonuclease Activity in Pancreatic Disease, Gastroenterologia Japonica, vol. 14, pp. 436-440, 1979.

Gannushikina, I.V., et al., Plasma DNA Levels in Patients with Atherosclerotic Involvement of the Major Arteries of the Head and lateral Amyotrophic Sclerosis, Bulletin of Experimental Biology and Medicine, vol. 124, No. 12, pp. 1164-1166, 1997 (Translated from: Gannushkina I.V. et al., Uroven DNK v plazme krovi bolnykh s 1-4 ateroskleroticheskim porazheniem magistralnykh artery golovy i bokovym amiotroficheskim sklerozom Byulleten'Experimental'noi Biologii i Meditsiny, Moscow, Meditsina, No. 12, pp. 610-612, 1997).

Gannushkina I.V. et al., Uroven DNK v plazme krovi bolnykh s 1-4 ateroskleroticheskim porazheniem magistralnykh artery golovy i bokovym amiotroficheskim sklerozom Bjulleten experimentalnoi biologii i meditsiny. Moscow, Meditsina, No. 12, pp. 610-612, 1997.

Gibbs et al., Mechanism-Based Target Identification and Drug Discovery in Cancer Research Science, vol. 287, pp. 1969-1973, 2000.

Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).

Gormally et al., Circulating free DNA in plasma or serum as biomarker of carcinogenesis: Practical aspects and biological significance, Mutation Research, vol. 635, pp. 105-117, 2007.

Gorrini, C., et al., Effect of apoptogenic stimuli on colon carcinoma cell lines with a different c-myc expression level, Int J Mol Med, vol. 11, pp. 737-742, 2003.

Gura, T., Systems for Identifying New Drugs Are Often Faulty, Science, vol. 278, pp. 1041-1042, 1997.

Hann, et al. Building 'validated' mouse models of human cancer. Curr Opin Cell Biol, 13(6), pp. 778-784, 2001.

Holterhus, Paul-Martin et al., Mosaicism due to a Somatic Mutation of the Androgen Receptor Gene Determines Phenotype in Androgen Insensitivity Syndrome, Journal of Clinical Endocrinology and Metabolism, vol. 82, No. 11, pp. 3584-3589, 1997.

Horlitz, Martin et al., Optimized Quantification of Fragmented, Free Circulating DNA in Human Blood Plasma Using a Calibrated Duplex Real-Time PCR, PLoS ONE, vol. 4, Issue 9, e7207, 2009.

Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.

International Search Report for PCT/RU2003/000304, mailed on Mar. 25, 2004.

International Search Report for PCT/RU2004/000260, mailed on Dec. 9, 2004.

International Search Report for PCT/RU2004/000261, mailed on Oct. 21, 2004.

International Search Report for PCT/RU2004/000262, mailed on Oct. 21, 2004.

International Search Report for PCT/RU2005/000236, mailed on Nov. 24, 2005.

International Search Report for PCT/RU2006/000642, mailed on Aug. 2, 2007.

Juncosa, Barbara, DNA on the Loose: Next-Gen Blood Tests Tap Free-Floating Genetic Material, Scientific American, Mar. 18, 2009.

Jylhava et al., Aging is associated with quantitative and qualitative changes in circulating cell-free DNA: the Vitality 90+ study, Mechanisms of Ageing and Development, vol. 132, pp. 20-26, 2011.

(56) References Cited

OTHER PUBLICATIONS

Kalandarishvili F., Nakoplenie spontanno povrezhdennoj DNK v ne- i postgepatjektomirovannoj pecheni u staryh krys, Med. Novosti Gruzii, No. 5, pp. 11-12, 1998 (Reference in Russian and English-language translation).

Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (reference in Russian and English-language translation).

Kawane, K, et al., DNAse II deficiency causes chronic polyarthritis in mice, Nature Clinical Practice Rheumatology, vol. 3, No. 4, p. 192, 2007.

Krapf F. et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.

Lachmann PJ, Lupus and Desoxyribonuclease, Lupus, vol. 12, pp. 202-206, 2003.

Lecompte, et al., Detection of free-circulating tumor-associated DNA in plasma of colorectal cancer patients and its association with prognosis, Int. J. Cancer, vol. 100, pp. 542-548, 2002.

Lee, D., Continued Marketing of a Useless Drug ('Varidase') in Panama, Lancet, Mar., vol. 335, p. 667, 1990.

Leland et al., Cancer chemotherapy—ribonucleases to the rescue, Chem. & Bio., vol. 8, pp. 405-413, 2001.

Leon et al., Free DNA in the Serum of Cancer Patients and the Effect of Therapy, Cancer Research, vol. 37, pp. 646-650, 1977.

Whitchurch, et al., Extracellular DNA Required for Bacterial Biofilm Formation, Science, vol. 295, p. 1487, 2002.

Yastrebova N.E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-Language translation).

Yasuda, Toshihiro et al., Activity Measurement for Deoxyribonucleases I and II with Picogram Sensitivity Based on DNA/SYBR Green I Fluorescence, Analytical Biochemistry, vol. 255, pp. 274-278, 1998.

Ye et al., Quantification of Circulating Cell-Free DNA in the Serum of Patients with Obstructive Sleep Apnea-Hypopnea Syndrome, Lung, vol. 188, pp. 469-474, 2010.

Zaman, et al., Direct amplification of Entamoeba histolytica DNA from amoebic liver abscess pus using polymerase chain reaction, Parasitol. Res., vol. 86, pp. 724-728, 2000.

Zaravinos et al., Levosimendan reduces plasma cell-free DNA levels in patients with ischemic cardiomyopathy, J. Thromb. Thrombolysis, vol. 31, pp. 180-187, 2011.

Zhong et al., Presence of mitochondrial tRNA(leu(UUR) A to G 3243 mutation in DNA extracted from serum and plasma of patients with type A 2 diabetes mellitus. J. Clin. Pathol., vol. 53, pp. 466-469, 2000.

Sugihara et al., Deoxyribonuclease treatment prevents blood-borne lier metastasis of cutaneously transplanted tumor cells in mice, Br. J. Cancer (67), pp. 66-70, 1993.

Li et al., The Haemophilus ducreyi cytolethal distending toxin activates sensors of DNA damage and repair complexes in proliferating and non-proliferating cells, Cellular Microbiology, vol. 4, pp. 87-99, 2002.

Liggett et al. , Methylation patterns of cell-free plasma DNA in relapsing-remitting multiple sclerosis, Journal of Neurological Sciences, vol. 290, pp. 16-21, 2010.

Macanovic et al., The treatment of systemic lupus erythematosus (SLE) in NZB/W FI hybrid mice; studies with recombinant murine DNase and with dexamethasone. Clinical and Experimental Immunology (106), pp. 243-252, 1996.

Malickova, Karin et al., Decreased Activity of DNase-I Predisposes to Immune-Mediated Complications in TBD Patients During Anti-TNFA Treatment, Gastroenterology, Abstract 202, vol. 138 (5 Supplement 1), S-37, 2010.

Maurer, HR, Bromelain: biochemistry, pharmacology and medical use, Cell Mol. Life. Sci., vol. 58, pp. 1234-1245, 2001.

Mel'nikov D, et al., Voprosy onkologicheskoi pomoschi na etape reformirovaniya zdravookhraneniya, Ekaterinburg, pp. 159-161, 1996 (Reference in Russian and English-language translation).

Merkus et al., DNase treatment for atelectasis in infants with severe respiratory syncytial virus bronchiolitis, Eur Respir J, vol. 18, pp. 734-737, 2001.

Moreira VG et al., Usefulness of cell-free plasma DNA, procalcitonin and C-reactive protein as markers of infection in febrile patients, Annals of Clinical Biochemistry, vol. 47, pp. 253-258, 2010.

Mosca et al., Cell-free DNA in the plasma of patients with systemic sclerosis, Clinical Rheumatology, vol. 28, pp. 1437-1440, 2009.

Mutirangura A., Serum/plasma viral DNA: mechanisms and diagnostic applications to nasopharyngeal an cervical carcinoma, Ann NY Acad Sci., vol. 945, pp. 59-67, 2001.

Nestle & Roberts, An extracellular nuclease from Serratia marcescens, J. Biol. Chem., vol. 244, pp. 5213-5218, 1969.

Ngan et al., Remarkable Application of Serum EBV EBER-1 in Monitoring Response of Nasopharyngeal Cancer Patients to Salvage Chemotherapy, Ann. NY Acad. Sci., vol. 945, pp. 73-79, 2001.

Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).

Oliven et al., Orally and Rectally Administered Streptokinase, Pharmacology, vol. 22, pp. 135-138, 1981.

Osivac et al., Reorganizacija DNK i biologicheskoje starenije, Biohimija, vol. 62, pp. 1491-1502, 1997 (Reference in Russian and English-language translation).

Perel'man MI, et al., Molekuljarnaja medicina i lechenie tuberkuleza, Problemi tuberkuleza, No. 5, pp. 5-7, 2001 (Reference in Russian and English-language translation).

Pisetsky, D., Immune response to DNA in systemic lupus erythematosus, Isr. Med. Assoc. J., vol. 3, pp. 850-853, 2001.

Pressler T., Review of recombinant human deoxyribonuclease (rhDNase) in the management of patients with cystic fibrosis, Biologics: Targets & Therapy, vol. 2, pp. 611-617, 2008.

Prince, W.S., et al, Pharmacodynamics of recombinant human DNase I in serum, Clin Exp Immunol, vol. 113, pp. 289-296, 1998.

Pulmozyme® (dornase alfa) Inhalation Solution product leaflet, Genetech, Inc., 2005.

Rao KS and Shrivastaw KP, Studies on the synthesis and degradation of DNA in developing and old chick cerebellum, Journal of Neurochemistry, vol. 27, pp. 1205-1210, 1976.

Raz E. et al., Anti-DNA antibodies bind directly to renal antigens and induce kidney dysfunction in the isolated perfused rat kidney, J Immunol , vol. 142, pp. 3076-3082, 1989.

Ross, Kenneth Andrew, Evidence for somatic gene conversion and deletion in bipolar disorder, Crohn's disease, coronary artery disease, hypertension, rheumatoid arthritis, type-1 diabetes, and type-2 diabetes, BMC Medicine, vol. 9, No. 12, pp. 1-29, 2011.

Roche, Pulmozyme®, Dornase alfa solution for inhalation 1.0 mg/ml, Data Sheet, 2008.

Schapira, Anthony H. V., Mitochondrial disease, Lancet, vol. 368, pp. 70-82, 2006.

Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).

Shak et al., Recombinant human DNAse I reduces the viscosity of cystic fibrosis sputum, Proc. Natl. Acad. Sci. USA, vol. 87, pp. 9188-9192, 1990.

(56) References Cited

OTHER PUBLICATIONS

Sherry et al., Presence and Significance of Desoxyribose Nucleoprotein in the Purulent Pleural Exudates of Patients, Proc, Soc. Exp. Biol. Med., pp. 179-184. 1948.
Shevchuk, N A., Vromyarazreshermiy Immunofluorcseentniy Analiz na DNK i Issialovanie Soderzhaniya DNK v Syvorotke Cheloveka, Voprosi Medicinskei Khimii, No. 4, 2001 (Reference in Russian and English Translation).
Shimony et al., Cell free DNA detected by a novel method in acute ST-elevation myocardial infarction patients, Acute Cardiac Care, vol. 12, pp. 109-111, 2010.
Sigma Product Information sheet for Deoxyribonuclease I from Bovine Pancreas.
Simpson G., et al., Successful treatment of empyerna thoracis with human recombinant deoxyribonuclease, Thorax, vol. 58, pp. 365-366, 2003.
Supplementary European Search Report for European Patent Appl. No. EP06843990, dated Nov. 23, 2009 and cf Form 1507.
Supplementary European Search Report for European Patent Appl. No. EP04748955, mailed May 19, 2009.
Supplementary European Search Report for European Patent Appl. No. EP04775224, mailed Oct. 28, 2009.
Supplementary European Search Report for European Patent Appl. No. EP05745412, dated Jul. 10, 2009.
Supplementary European Search Report for European Patent Appl. No. EP03796243, dated Jan. 12, 2010.
Tetz VV and Tetz GV, Effect of Extracellular DNA Destruction by DNase I on Characteristics of Forming Biofilms, DNA and Cell Biology, vol. 29, pp. 399-405, 2010.
Tetz, GV, et al., Effect of DNase and Antibiotics on Biofilm Characteristics, Antimicrobial Agents and Chemotherapy, vol. 53, pp. 1204-1209, 2009.
Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.
Translation of International Preliminary Report on Patentability for PCT/RU2003/000304, dated Nov. 1, 2005.
Translation of International Preliminary Report on Patentability for PCT/RU2004/000260, mailed Jan. 14, 2006.
Translation of International Preliminary Report on Patentability for PCT/RU2004/000261, mailed Dec. 2, 2005.
Translation of International Preliminary Report on Patentability for PCT/RU2004/000262, mailed Apr. 12, 2006.
Translation of International Preliminary Report on Patentability for PCT/RU2005/000236, mailed Feb. 13, 2008.
Translation of International Preliminary Report on Patentability for PCT/RU2006/000642, dated Jul. 7, 2009.
Ulrich & Friend, Toxicogenomics and drug discovery: will new technologies help us produce better drugs? Nature, vol. 1, pp. 84-88, 2002.
Varidase Buccal Tablets product information from Lederle Laboratories Inc., Canad. M. A. J., vol. 84, pp. 867-868, 1961.
Varidase product information from EPGOnline, accessed on Dec. 12, 2011.
Vonmoos, P.L. and Straub, P.W., Absorption and hematologic effect of streptokinase-streptodornase (varidase) after intracavital or oral administration, Schweiz Med Wochenschr, vol. 109, pp. 1538-1544,1979, Abstract.
Arinchina, et al., "Cellular and Humoral Mechanisms of Immunity Changing", Ageing biology, Physiology (1982), pp. 280-282 and English translation thereof.
Campisi, Judith, "Cancer and Ageing: Rival Demons?", Nature Reviews/Cancer (2003), pp. 339-349.
Campisi, Judith et al. "Cellular Senescence: When Bad Things Happen to Good Cells", Nature Reviews/Molecular Cell Biology (2007), vol. 08, pp. 729-740.
Canudas-Romo, Vladimir, "Three Measures of Longevity: Time Trends and Record Values", Demography (2010), vol. 47, No. 02, pp. 299-312.

Coppe, Jean-Philippe et al., "Secretion of Vascular Endothelial Growth Factor by Primary Human Fibroblasts at Senescence", The Journal of Biological Chemistry (2006), vol. 281, No. 40, pp. 29568-29574.
Gal S. and Wainscoats, "Detection and Quantitation of Circulating Plasmodium falciparum DNA by Polymerase Chain Reaction", Methods in Molecular Biology (2006), vol. 336, pp. 155-162.
Gibson, R. L. et al., "Pathophysiology and management of pulmonary infections in cystic fibrosis.", Am J. Respir Crit Care Med (2003), vol. 168, pp. 918-951.
Harley, Calvin B., "Telomere Loss: Miotic Clock or Genetic Time Bomb?", Mutation Research (1991), vol. 256, pp. 271-281.
Hayflick, L., "Aging Under Glass", Dept. of Medical Microbiology, Stanford University School of Medicine, Exp. Geront. (1970), vol. 05, pp. 291-303.
Hayflick, L., "The Limited in Vitro Lifetime of Human Diploid Cell Strains", Experimental Cell Research (1965), vol. 37, pp. 614-635.
Hayflick, L. et al. "The Serial Cultivation of Human Diploid Cell Strains", Experimental Cell Research (1961), vol. 25, pp. 585-621.
Hursting, Stephen D. et al., "Calorie Restriction, Aging and Cancer Prevention: Mechanisms of Action and Applicability to Humans", Annu. Rev. Med. (2003), vol. 54, pp. 131-152.
Irvine, D. Stewart et al., "DNA Integrity in Human Spermatozoa: Relationships with Semen Quality", Journal of Andrology (2000), vol. 21, No. 01, pp. 33-44.
Kagan, Valerian E. et al., "Toward Mechanism-based Antioxidant Interventions", Lessons from Natural Antioxidants, Ann. New York Academy of Sciences 959 (2002), pp. 188-198.
Kenyon, Cynthia "A Conserved Regulatory System for Aging", Cell (2001), vol. 105, pp. 165-168.
Krtolica, Ana et al., "Senescent Fibroblasts Promote Epithelial Cell Growth and Tumorigenesis: A Link Between Cancer and Aging", PNAS (2001), vol. 98, No. 21, pp. 2072-12077.
Morton, C. O., et al., "Dynamics of extracellular release of Aspergillus furnigatus DNA and galactomannan during growth in blood and serum", J. Med. Microbiol. (2010), vol. 59, pp. 408-413.
Mueller V. and Schmit J., Fungal biodiversity: what do we know? What can we predict? Biodivers Conserv, (2007), vol. 16, pp. 1-5.
National Institute on Aging, "Can We Prevent Aging? Tips from the National Institute on Aging", (Feb. 2012), pp. 1-8.
Parrinello, Simona et al., "Stromal-epithelial Interactions in Aging and Cancer: Senescent Fibroblasts alter Epithelial Cell Differentiation", Journal of Science (2004), vol. 118, No. 03, pp. 485-496.
Riches, A. C. et al., "Blood Volume Determination in the Mouse", J. Physiol. (1973), vol. 228, pp. 279-284.
Robertson, D. et al., "The microbiology of the acute dental abscess", J. Med. Microbiol. (2009), vol. 58, pp. 155-162.
Rowe, et al., "WHO Manual for the Standardized Investigation and Diagnosis of the Infertile Couple", Cambridge University Press (1993), p. 83.
Rowlatt, C. et al., "Lifespan, Age Changes and Tumour Incidence in an Ageing C57BL Mouse Colony", Laboratory Animals (1976), vol. 10, pp. 419-442.
Schloss, Patrick D. et al., "Status of the microbial census", Microbial and Molecular Biology Reviews (2004), vol. 68, No. 04, pp. 686-691.
Schmitz, Kathryn H. et al., "The Intersection of Cancer and Aging: Establishing the Need for Breast Cancer Rehabilitation", Cancer Epidemiol Biomarkers Prev (2007); vol. 16, No. 05, pp. 866-872.
Shah, Pallav L. et al., Medium term treatment of stable stage cystic fibrosis with recombinant human DNase I, Thorax (1995), vol. 50, pp. 333-338.
Whitfield, J. F. et al., "The Effects of X-Radiation on Lactate Metabolism of Mammalian Cells", Experimental Cell Research (1965), vol. 37, pp. 637-649.
WHO Laboratory Manual for the Examination of Human Semen and Sperm-cervical Mucus Interaction, 4th ed., Cambridge University Press, (1999), p. 128.
Finlay, B. J. "The global diversity of protozoa and other small species", International Journal for Parasitology (1998), vol. 28, pp. 29-48.
European Office Action dated Jun. 12, 2013, which issued during the prosecution of European Patent Application No. 05745412.6.

(56) References Cited

OTHER PUBLICATIONS

Anker P. and Stroun M. "Tumor-related alterations in circulating DNA, potential for diagnosis, prognosis and detection of minimal residual disease", Leukemia (2001), vol. 15 pp. 289-291.
Translation of PCT International Preliminary Report on Patentability for PCT/RU2005/000236, mailed on Nov. 24, 2005.
Supplementary Partial European Search Report for Application No. EP04748955.4, dated May 19, 2009.
Scoble, J. E. et al., "Atherosclerotic renovascular disease causing renal impairment—a case for treatment", Clinical Nephrology (1989), vol. 31 No. 03, pp. 119-122.
Hakkim, Abdul et al., "Impairment of neutrophil extracellular trap degradation is associated with lupus nephritis", PNAS (2010), vol. 107, No. 21, pp. 9813-9818.

METHOD FOR TREATING SYSTEMIC DNA MUTATION DISEASE

CROSS-REFERENCE TO RELATED APPLICATIONS

This application is a Divisional of U.S. application Ser. No. 14/309,363, filed Jun. 19, 2014, now U.S. Pat. No. 9,463,223, which is a Continuation of U.S. application Ser. No. 13/772,499 filed Feb. 21, 2013, now U.S. Pat. No. 8,796,004, which is a Continuation of U.S. application Ser. No. 12/835,029 filed Jul. 13, 2010, now U.S. Pat. No. 8,388,951, which is a Continuation-in-Part of U.S. application Ser. No. 10/564,609 filed Jan. 12, 2006, now abandoned, which is a U.S. national phase application under 35 U.S.C. §371 of International Patent Application No. PCT/RU2004/000260, filed Jul. 1, 2004 (published in Russian on Jan. 20, 2005 as WO 2005/004789), which claims priority of Russian Federation Patent Application No. RU2004/08057, filed Mar. 12, 2004 and International Patent Application No. PCT/RU2003/000304 filed Jul. 14, 2003, all of which applications are incorporated by reference herein in their entireties.

BACKGROUND OF THE INVENTION

1. Field of the Invention

The present invention relates generally to medical treatment of the systemic DNA mutation diseases accompanied with development of somatic mosaicism and elevation of blood extracellular DNA and, more particularly, to a treatment of diabetes mellitus and atherosclerosis.

2. Description of the Related Art

Mosaicism refers to a mixture of cells of different genetic composition in one individual. When DNA mutation is detectable in number, but not all somatic cells in one individual, it is called somatic mosaicism. Development of somatic mosaicism has been recently recognized as important mechanism of systemic DNA mutation diseases progression (Gottlieb B et al., Selection and mutation in the "new" genetics: an emerging hypothesis, Hum Genet. 2010 March; 127(5): 491-501.) Importance of somatic mosaicism involving disease-causing mutations has been reported for variety of monogenic (reviewed by Youssoufian H., Nature Reviews Genetics 3, 748-758, October 2002) and more recently for multifactor DNA mutation diseases: cardiac rhythm disorders (M. H. Gollob et al., Somatic mutations in the connexin 40 gene (GJA5) in atrial fibrillation, N. Eng. J. Med. 354 (2006), pp. 2677-2688.); atherosclerosis (S. De Flora et al., Mutagenesis and cardiovascular diseases. Molecular mechanisms, risk factors, and protective factors, Mutat. Res. 621 (2007), pp. 5-17), systemic vascular disorders (B. Gottlieb et al., BAK1 gene variation and abdominal aortic aneurysms, Hum. Mutat. 30 (2009), pp. 1043-1047); immune deficiencies (Wada T. et al., Somatic mosaicism in primary immune deficiencies, Curr Opin Allergy Clin Immunol. 2008 December; 8(6): 510-4); Alzheimer disease (Beck J A et al., Somatic and germline mosaicism in sporadic early-onset Alzheimer's disease. Hum Mol Genet. 2004 Jun. 15; 13(12): 1219-24.); diabetes mellitus (Emma L. Edghill et al, Origin of de novo KCNJ11 mutations and risk of neonatal diabetes for subsequent siblings. The Journal of Clinical Endocrinology & Metabolism Vol. 92, No. 5 1773-1777).

According to current knowledge the systemic DNA mutation diseases represent very distinct subsets of human pathology different in etiology and pathogenesis and accordingly has fundamentally different, usually palliative treatment modalities-cholesterol lowering therapy for atherosclerosis (New Concepts and Paradigms in Cardiovascular Medicine: The Noninvasive Management of Coronary Artery Disease, K. Lance Gould, THE AMERICAN JOURNAL OF MEDICINE, Volume 104, Jun. 22, 1998, pp. 2-17) and insulin therapy or insulin sensitization therapy for diabetes mellitus (Pharmacological Management of Diabetes: Recent Progress and Future Perspective in Daily Drug Treatment, Gerard Emilien et al., Pharmacol. Ther. Vol. 81, No. 1, pp. 37-51, 1999).

More recently the gene therapy was recognized as potential tool for disease specific intervention which may target the function of certain specific disease involved genes and provide more efficient cure based on repair of existing genetic defects in atherosclerosis (Ishisaki A, et al., Novel ideas of gene therapy for atherosclerosis: modulation of cellular signal transduction of TGF-beta family. Curr Pharm Des. 2006; 12(7): 877-86; Harris J D, et al. ApoE gene therapy to treat hyperlipidemia and atherosclerosis. Curr Opin Mol Ther. 2006 August; 8(4): 275-87; Hayden et al. Gene therapy method for reducing risk of atherosclerosis, U.S. Pat. No. 6,784,162) and diabetes mellitus (G B Parsons, Ectopic expression of glucagon-like peptide 1 for gene therapy of type II diabetes, Gene Therapy (2007) 14, 38-48; L. Chan, In vivo gene therapy for diabetes mellitus, Trends in Molecular Medicine, Volume 9, Issue 10, October 2003, Pages 430-435; M. During, Compositions for gene therapy of diabetes, EP 1889914).

However no cure exists which may target the evolution of disease causing DNA mutations leading to development of somatic mosaicism. Accordingly, the development of new effective, non-toxic method that may suppress the development of somatic mosaicism and consequently be effective cure for systemic DNA mutation disease is an extremely important task.

Circulating extracellular nucleic acids were discovered more than 60 years ago (Anker P Circulating DNA in plasma or serum, Clin Chim Acta. 2001 November; 313(1-2): 143-6). However until now elevated levels of extracellular blood DNA in systemic DNA mutation diseases, and in particular in atherosclerosis and diabetes mellitus were considered only as useful diagnostic and research tool (El Tarhouny S. A. et al., Assessment of cell-free DNA with microvascular complication of type II diabetes mellitus, using PCR and ELISA. Nucleosides Nucleotides Nucleic Acids. 2010 March; 29(3): 228-36; Langford M P et al., Plasma levels of cell-free apoptotic DNA ladders and gamma-glutamyltranspeptidase (GGT) in diabetic children. Exp Biol Med (Maywood). 2007 October; 232(9): 1160-9; Arnalich F. et al., Prognostic value of cell-free plasma DNA in patients with cardiac arrest outside the hospital: an observational cohort study, Critical Care 2010, 14; Arnalich F. Association of cell-free plasma DNA with preoperative mortality in patients with suspected acute mesenteric ischemia, Clinica Chimica Acta, in press; Zhong S, Presence of mitochondrial tRNA (Leu (UUR)) A to G 3243 mutation in DNA extracted from serum and plasma of patients with type 2 diabetes mellitus 2000 June; 53(6): 466-9.)

Circulating extracellular nucleic acids have never been considered as potential therapeutic target in systemic DNA mutation diseases. Accordingly, no therapeutic method was developed which targets extracellular blood DNA in systemic DNA mutation diseases. Thus it makes impossible to take any technical solution as prototype.

As used in this application, the following terms are meant to have the following corresponding definitions.

Deoxyribonuclease (DNASE) is any enzyme that catalyzes the hydrolytic cleavage of phosphodiester linkages in the DNA backbone.

Extracellular blood DNA number average molecular weight—the number average molecular weight is a way of determining the molecular weight of a polymer. The number average molecular weight is the ordinary arithmetic mean or average of the molecular weights of the individual DNA macromolecules. It is determined by measuring the molecular weight of n polymer molecules, summing the weights, and dividing by n. The number average molecular weight of extracellular blood DNA can be determined by gel electrophoresis. The shift of extracellular blood DNA bands to low-MW areas reflect decrease number average molecular weight and in fact reflects enzymatic cleavage of extracellular blood DNA.

DNA mutation disease refers to diseases where specific DNA mutation has been identified as single leading cause (monogenic or single gene disorders) or multifactor disorders resulting from mutations in multiple genes, often coupled with environmental causes.

Systemic disease is one that affects a number of organs and tissues, or affects the body as a whole.

SUMMARY OF THE INVENTION

The object of this invention is to develop high-performance and low-toxic method for treatment of systemic DNA mutation diseases accompanied with development of somatic mosaicism and elevation of blood extracellular DNA and, more particularly, to a treatment of diabetes mellitus and atherosclerosis.

According to the invention this task is resolved by introducing a treatment agent into a circulating blood system of a patient diagnosed with systemic DNA mutation disease when said treatment agent destroys extracellular DNA in said blood of said patient and wherein said treatment agent used to destroy said extracellular DNA is a DNASE enzyme. In one of preferred embodiments said agent must be administered in doses and regimens which sufficient to decrease number average molecular weight of circulating extracellular blood DNA in the blood of said patient; such decrease of number average molecular weight might be measured by gel electrophoresis of extracellular blood DNA fraction from the blood of said patient. In one of preferred embodiments the method according the invention can be effectively applied for treatment of diabetes mellitus and atherosclerosis. A DNASE enzyme may be further applied in a dose and regime that results in a DNA hydrolytic activity measured in blood plasma that exceeding 1.5 Kunitz units per 1 ml of blood plasma for more than 12 hours within a period of 24 hours.

The present invention suggests that systemic DNA mutation disease can be treated by reducing of circulating extracellular blood DNA levels.

Development of systemic DNA mutation disease in humans is accompanied by quantitative and/or qualitative change of blood extracellular DNA.

There are no analysis of blood extracellular DNA spectrum and its biological role in systemic DNA mutation disease prior to this invention. A search of the prior art reveals no published data concerning an analysis of blood extracellular DNA spectrum in systemic DNA mutation disease performed by direct cloning and without use of polymerase chain reaction (PCR). PCR can pervert a pattern of blood extracellular DNA because of specificity of primers used for amplification. There is no available knowledge about genetic repertoire of extracellular blood DNA in patients suffering from systemic DNA mutation disease and about biological role of extracellular blood DNA in course of these diseases. Nothing is known about potential therapeutic value of extracellular blood DNA enzymatic destruction for treatment of systemic DNA mutation disease; so, taking into account all aforesaid, the invention complies with requirements of "novelty" criteria (N).

As the applicant established by direct cloning and sequencing of extracellular blood DNA without PCR (Polymerase Chain Reaction), the extracellular blood DNA of patients with systemic DNA mutation disease contains the unique quantitative and qualitative repertoire of genes, which non-randomly represents human genome and contains genetic elements involved in to the development of the disease. It was shown that extracellular blood DNA might promote the development of somatic mosaicism and systemic DNA mutation disease.

It was established that enzymatic destruction of extracellular blood DNA by DNASE enzyme when applied in certain surprisingly high specific doses has significant therapeutic effect on the course of systemic DNA mutation disease.

Aforesaid new characteristics of the claimed invention are based on new ideas about mechanism of development of systemic DNA mutation disease. In this way the claimed method conformances to requirements of "invention step" criteria (IS).

BRIEF DESCRIPTION OF THE DRAWINGS

The advantages and features of the present invention have been explained by detailed description of embodiments with references to drawings.

DESCRIPTION OF THE PREFERRED EMBODIMENTS

Figure 1:
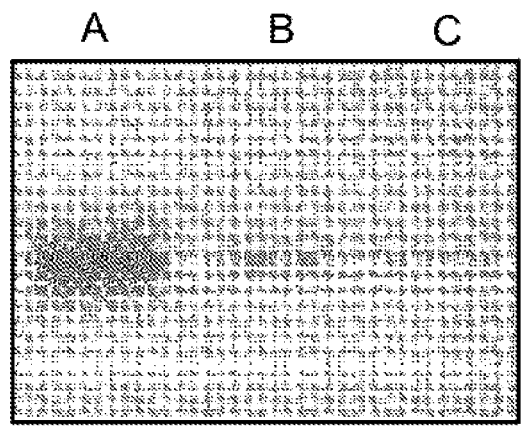
FIG. 1: NF-kappa B expression in (A) cultured aortic endothelial cells treated with extracellular blood DNA fraction from patient suffering from systemic atherosclerosis; (B) cultured aortic endothelial cells treated with extracellular blood DNA fraction from patient suffering from systemic atherosclerosis plus 1 mkg/ml of DNASE1; and (C) control cells.

The inventive method is realized as follows:

Materials and Methods:

The following agents, which destroy extracellular blood DNA, were used: bovine pancreatic DNASE (Sigma, specific activity 2 400 Kunitz units/mg; Samson-Med, specific activity 1 500 Kunitz units/mg), recombinant human DNASE 1 (Gentech, specific activity 1000 U/mg).

Extracellular DNA from blood plasma was isolated as follows: fresh plasma (no more than 3-4 hours after sampling) with anticoagulant (sodium citrate) was centrifuged on Ficoll-Plaque Plus (Amersham-Pharmacia) during 20 minutes at 1500 g. at room temperature. ½ of plasma was detached, not affecting the rest of cells on the Ficoll pillow, and further centrifuged at 10000 g. during 30 min for separation from cell fragments and debris. Supernatant was detached, without affecting of the sediment, and was toped up to 1% of sarkosil, 50 mM tris-HCl, pH 7.6, 20 mM EDTA, 400 mM NaCl, and then mixed with equal volume of phenol-chloroform (1:1) mixture. The prepared emulsion was incubated during 2 hours at t=65° C., then phenol-chloroform mixture was separated by centrifuging (500 g during 20 minutes, room temperature). The procedure of deproteinization with phenol-chlorophorm mixture was repeated 3 times, and then the water phase was processed with chloroform and diethyl ether. Separation from organic solvents was made by centrifugation at 5000 g during 15 minutes. Then equal volume of izopropanol was added to resulting aqueous phase and the mixture was incubated overnight at 0° C. After sedimentation the nucleic acids were separated by centrifugation at 10000 g during 30 minutes. The sediment of nucleic acids was dissolved in of 10 mM tris-HCl buffer, pH 7, 6 with 5 mM EDTA, and inflicted to the CsCl gradient (1M, 2.5M, 5.7M) in test-tube for rotor SW60Ti. The volume of DNA solution was 2 ml, volume of each step of CsCl was 1 ml. Ultracentrifugation was conducted in L80-80 (Beckman) centrifuge during 3 hours at 250000 g. DNA was collected from the surface of each gradient step into fractions. These fractions were dialyzed during 12 hours (t=4° C.) and pooled. Presence of DNA in fractions was determined by agar electrophoresis and DNA was visualized by ethidium bromide staining. The amount of DNA was determined with spectrophotometer (Beckman DU70) in cuvetts (100 mkl) at wavelength of 220-230 nm.

NOD mice were obtained from <<Pushcino>> animal breeding house.

Example 1. DNASE Treatment Suppresses the Development of Somatic Mosaicism

Frequency of HPRT gene's mutations in blood T-lymphocytes was studied as the model of development of somatic mosaicism in vivo. The human HPRT gene, mapped to chromosome Xq26, codes for a constitutively expressed, but non-essential, enzyme involved in purine metabolism. Mutant peripheral blood T-lymphocytes which do not express a functional HPRT gene product can be enumerated and clonally expanded by selective growth in the normally toxic purine analog 6-thioguanine in the presence of specific mitogens and growth factors. In normal, unexposed individuals the frequency of 6-thioguanine resistant T-lymphocytes is typically $10^{-6}$ to $10^{-5}$ (R. J. Albertini, J. A. Nicklas, J. P. O'Neill, S. H. Robison, In vivo somatic mutations in humans: measurement and analysis, Annu. Rev. Genet. 24 1990. 305-326.) Molecular analyses of the mutant, HPRT deficient, clones have demonstrated that 85% of the gene inactivating mutations observed in unexposed adults arises by localized HPRT gene alterations-single base changes, small deletions or insertions and frame shift.

Selective lymphocyte cloning was performed using peripheral blood of 8 female patients with different forms of advanced cancer who got surgical resection at Kostushko municipal Hospital (St. Petersburg) and immunomodulation therapy at neoadjuvant setting (Neovir, 250 mg IM once every 2 days for 3 weeks). Following surgical resection 4 patients were further treated by IV infusions of bovine pancreatic DNASE (Samson) according the following schedule: 2000 mkg/kg×4 times daily for 21 day. Following completion of treatment the patients were assayed for HPRT (−) mutation in blood lymphocytes.

Mononuclear cells were isolated from the whole blood samples using Ficoll-Paquee (Becton Dickinson). Mitogenic stimulation of the separated lymphocytes ($1\times10^6$/ml) was initiated with 1 mg/ml phytohemagglutinin (PHA) in RPMI 1640 media supplemented with penicillin (100 U/ml), streptomycin (100 mg/ml), 20% nutrient medium HL-1 and 5% BSA at 5% $CO_2$ at 37° C. for 24 h. Following wash the cells were then seeded in 96-well round-bottomed plates at cell density of $2\times10^4$ cells per well in selection medium to determine cloning efficiency. The cells were plated in 200 ml of the RPMI medium containing 1 mg/ml 6-thioguanine, 0.125 mg/ml PHA, 20% HL-1 and 5% BSA supplemented with interleukin-2 (BD Biosciences, 10 BRMP units/mi). Four 96-well plates were seeded for each patient. After 5 days of culture, the colonies on mutant selection plates were scored for growth using an inverted microscope.

The results of selective T-lymphocyte cloning are presented in the table below:

| Patient | Treatment | Total number of wells | HPRT wells (growth positive) |
|---|---|---|---|
| KNP | DNASE | 384 | 7 |
| PGP | DNASE | 384 | 12 |
| BAI | DNASE | 384 | 2 |
| FVV | DNASE | 384 | 11 |
| SLS | NO | 384 | 47 |
| GAN | NO | 384 | 22 |
| PMI | NO | 384 | 31 |
| ENV | NO | 384 | 55 |

Thus, inventive treatment suppresses spread of HPRT (−) mutation and suppresses the development of somatic mosaicism.

Example 2. Extracellular Blood DNA Promotes the Development of Somatic Mosaicism The extracellular blood plasma DNA was purified from blood of patient ENV as specified in methods section. Mononuclear cells were isolated from the whole blood samples of patients KNP, PGP, BAI and FW as specified in Example 1. The mitogenic stimulation and selective cloning were performed as specified in Example 1 with modification as follows: during mitogenic activation stage lymphocyte cultures of patients KNP, PGP, BAI and FW were supplemented with 50 mkg/ml of extracellular blood plasma DNA purified from patient ENV. After 5 days of culture, the colonies on mutant selection plates were scored for growth using an inverted microscope. The results of selective T-lymphocyte cloning are presented in the table below:

| Patient | Total number of wells | HPRT wells (growth positive) |
|---|---|---|
| KNP | 384 | 18 |
| PGP | 384 | 15 |
| BAI | 384 | 21 |
| FVV | 384 | 31 |

Thus, extracellular blood DNA promotes the development of somatic mosaicism.

Example 3. Sequencing of Extracellular Blood DNA from the Patient Suffering from Type 2 Diabetes and Systemic Atherosclerosis. Treatment of Atherosclerosis A 54-year-old man has been admitted to the Cardiothoracic surgery department of Kostushko municipal hospital (St. Petersburg) in severe condition complaining on intensive pain in abdomen, diarrhea, intensive pain in legs that appear during walking, loss of weight. Diabetes mellitus type 2 was diagnosed 12 years ago and glybencamide was prescribed. Pain in epigastrium after food intake appeared 15 months ago. Antacids were prescribed but pain continued to increase and steatorrhea appeared in the last 3 months. Because of intensive pain syndrome anorexia has developed in a couple of days prior admittance. Considerable exhaustion (body weight was 44 kg; body weight loss was 28 kg for the last 5 months) and absence of arterial pulsation on legs were found out during examination. No organic changes were observed during gastroduodenoscopy and colonoscopy. Electrocardiographic data was not changed pathologically. Moderate increase of cholesterol level and low-density lipoprotein fraction was observed in blood analysis. Glycated hemoglobin' level was 11%. Partial occlusion of aorta below renal artery (70%), partial occlusion of iliac arteries (90%), total occlusion of upper and lower mesenteric artery were observed on aortography.

The probes of patient's extracellular blood DNA were taken before initiation and on day 35 of therapy. The extracellular DNA was cloned by the method which allows to get non amplified plasmid libraries of blood extracellular DNA with representativeness up to one million of clones with the average size of 300-500 base pairs. The DNA which has been isolated using the protocol specified in Materials and Methods section was treated with Proteinase K (Sigma) at 65° C. and subjected to additional phenol-chloroform extraction step with further overnight precipitation by ethanol. The DNA fraction was than treated by Eco RI restrictase or by Pfu polymerase (Stratagene) in presence of 300 mkM of all desoxynucleotidetriphosphates for sticky-ends elimination. The completed DNA was phosphorylated by polynucleotidkinase T4 and ligated to pBluescript plasmid (Stratagene), which had been digested with EcoRI or PvuII and dephosphorylated by phosphatase CIP (Fermentas). The process of ligation was conducted with Rapid Legation Kit (Roche). The ligated library was transformed into DH12S cells (Life Technologies) by electroporation (*E. coli* porator; BioRad). 12-20 electroporation covets were used for the transformation of one library. The library serial dilutions were cloned on 1.5% agar and LB media supplemented with ampicillin. In both cases the libraries represented 2-3×10$^6$ clones.

Analysis of 75 randomly selected clones with the size 300-1000 base pairs from the "before treatment" library revealed 56 clones containing unique human DNA sequences as presented at the table below:

| Gene | Number of clones | Potential role in Atheroscleros is/diabetes mellitus |
|---|---|---|
| Neutral endopeptidase | 2 | At atherosclerosis its activity is increased in endothelial cells, nonstriated muscle cells, stromal cells of artery' intima. Decreasing of its activity can decrease lipids accumulation in vessels wall. |
| Muskelin 1 | 1 | Works as mediator of cell response on thrombospondin 1. Thrombospondin 1 - mediated processes are pathophysiological components of |

-continued

| Gene | Number of clones | Potential role in Atheroscleros is/diabetes mellitus |
|---|---|---|
| | | atherosclerotic affection of artery wall. |
| Nf-kappaB | 3 | At hyperglycemia and atherosclerosis activity is increased in cells of artery wall. |
| E-selectin | 3 | High level of expression is a risk factor of angiopathy development at diabetes type 2. |
| GAD2: glutamate 2 decarboxylase 2 | 2 | One of the main pancreatic autoantigens. |
| Phospholipase C, epsilon | 2 | Induces expression of receptors of low-density lipoproteins |
| BAI3: brain-specific angiogenesis inhibitor | 1 | Angiogenesis inhibitor |
| Nicotinamide nucleotide transhydrogenase | 1 | Involved in detoxification of reactive oxygen species and insulin secretion. |
| 17 kD fetal brain protein | 1 | UNCLEAR |
| CRTL1: cartilage linking protein 1 | 1 | Involved in morphogenetic process in heart and large vessels |
| Transient receptor potential cation channel | 1 | UNCLEAR |

Thus, extracellular blood DNA from patient having diabetes mellitus and systemic atherosclerosis contains significant non-random presence of human disease-relevant unique genomic DNA.

Patient was considered as not eligible for surgery so, conservative therapy was chosen. Intensive IV nutrition was started. Insulin and anti-aggregation therapy have being started. Under patient consent daily intravenous infusions of bovine pancreatic DNASE (Samson) at daily dose of 800 mg (1 200 000 Kuntz units) divided to 4 two-hour deliveries were started. Week after start of DNASE therapy pain syndrome disappeared and patient was allowed to take light dietetic food orally. 20 days after start of DNASE treatment patient was switched to full value oral nutrition. General state was improved, body weight has increased. 45 days following initiation of DNASE treatment patient was reexamined by angiography. 20% decrease of aorta occlusion and 35% decrease of iliac artery occlusion level as well as appearance of blood circulation in upper and lower mesenteric was observed. Patient was considered as eligible for revascularization surgery.

Extracellular blood plasma DNA sampled from patients blood at day 35 following start of DNASE therapy was assayed by gel electrophoresis and cloning. Analysis of 50 clones randomly chosen from the library obtained from the extracellular blood plasma DNA of patient on the day 35 after the beginning of treatment has shown that more than 90% of revealed clone sequences are short fragments of repetitive human DNA with the dominance of alpha-satellite DNA.

Example 4. Influence of Extracellular Blood DNA from the Patient with Systemic Atherosclerosis on Disease Causing Protein Expression in Aortic Endothelial Cells Endothelial NF-kappa B signaling orchestrates proinflammatory gene expression at the arterial wall and promotes the pathogenesis of atherosclerosis. Here we assayed the influence of extracellular blood DNA from the patient diagnosed with systemic atherosclerosis on NF kappa B expression in primary aorta endothelial cell culture. Blood plasma was obtained from vascular surgery clinic of St. Petersburg Medical Academy from the patient undergoing femoro-femoral bypass surgery due to severe atherosclerotic arterial occlusion.

The extracellular blood DNA was purified as described in Materials and Methods section. The aortic endothelial cells (C-006-5C; Invitogen) were plated at density of $5\text{-}8\times10^2$ cells/mm$^2$ in multiwell (12×) cell culture plates in Clonetics® EGM®-2MV media (Lonza Cologne AG) and incubated for 48 h. at 37° C. and 5% $CO_2$. Following 24 h of growth the culture media was supplemented with 50 mkg/ml of patient extracellular blood DNA fraction or 50 mkg/ml of patient extracellular blood DNA fraction plus human recombinant DNASE-1 (Genentech) at 1 mkg/ml concentration.

After 24 h. culturing the explants were lysed in buffer containing 20 mM Tris-HCl, 150 mM NaCl, 1 mM phenylmethylsulfonylfluoride, 5 mg/ml aprotinin, 0.5% Nonidet P-40 (Sigma-Aldrich) for 1 hour at 4° C. The lysates were centrifuged for 10 min at 20,000 rpm. The supernatants were diluted with reducing sample buffer and were separated by electrophoresis on a 10% SDS-PAGE gel (20 mkg protein per lane loaded). The proteins were transferred onto Hybond-C-nitrocellulose membrane (Amersham Italia, Milan, Italy. For immunoblot analysis, the membranes were incubated with the NF-.kappa.B antibodies (Stressgen). The bands were detected using the chemiluminescence system.

The results are presented at the FIG. 1. Extracellular blood DNA fraction from patient suffering from systemic atherosclerosis increases the expression of NF-kappa B in cultured aortic endothelial cells and treatment with DNASE ameliorate this effect.

Example 5. Treatment of Diabetes Mellitus

Figure 2A:
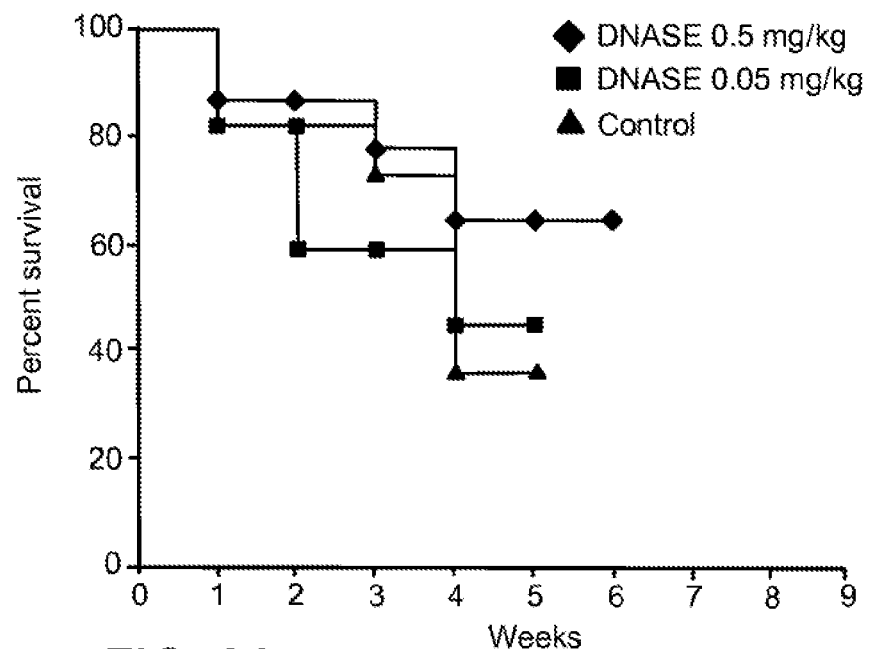
FIGS. 2A-2B: Panel 2A shows a graph of the survival of NOD diabetic mice treated with different doses of DNASE1—50 mkg/kg, 500 mkg/kg, and control; Panel 2B shows average molecular weight of extracellular blood plasma DNA (as measured by electrophoresis) in blood of NOD diabetic mice treated with 50 mkg/kg DNASE 1 (A), 500 mkg/kg DNASE1 (B), and control (C).
Figure 2B:
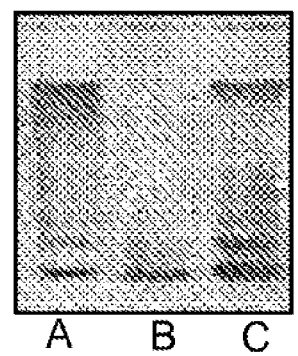

Non-obese diabetic (NOD) mice exhibit a susceptibility to spontaneous development of autoimmune insulin dependent diabetes mellitus. 60 NOD mice were recruited to the study at the age of 14 weeks when all of them became hyperglycemic. The recombinant human DNASE 1 (Gentech) at 50 mkg/kg and 500 mkg/kg was administered intramuscularly twice daily for 21 day. 2 mice from each group were sacrificed at the last treatment day to perform evaluation of extracellular blood plasma DNA. The efficacies of DNASE were assessed based on the survival rate at day 35. The results of experiments are presented at the FIG. 2. There is evident increase in survival of mice treated with 500 mkg/kg DNASE 1; such survival is accompanied with decrease of average molecular weight of extracellular blood plasma DNA (as measured by electrophoresis) in blood of NOD diabetic mice. Thus, high doses of DNASE according to inventive treatment are able to decrease the quantities of circulating extracellular blood plasma DNA and are effective against systemic DNA mutation disease-diabetes mellitus.

Example 6. Treatment of Diabetes Mellitus

A 46-years-old patient with 3 years history of type 2 diabetes mellitus was admitted to the internal therapy clinic of St. Petersburg Medical Academy. Patient failed to achieve proper glucose control using oral hypoglycemic agents including those of thiazolidinediones, biguanides and sulfonylureas. Patient was switched to 0.3 IU/kg of NPH insulin monotherapy (21 IU daily) and discharged from clinics under the supervision of ambulatory endocrinologist.

Three month later patient was readmitted to the clinic since glycosylated hemoglobin (HbA1) level was still too high (above 10%) with evolving microalbuminuria and decrease in vision sharpness despite daily insulin dose was adjusted up to 1.2 U/kg (84 U/day) during ambulatory period. Under patient consent he was assigned for intramuscular injections of bovine pancreatic DNASE (Samson) twice daily at 200 mg/day dose for 4 months and again discharged from clinics. At 4 month after initiation of treatment patient were reexamined in clinics outpatient department. Significant improvement in insulin sensitivity, improvement of glycemia control and normalization of kidney function has been reported by patient ambulatory endocrinologist and confirmed by laboratory examination in clinic. The effect of DNASE treatment on patient disease indicators is presented in table below:

| Indicator | Prior DNASE treatment | At DNASE course completion |
| --- | --- | --- |
| Insulin requirement | 1.2 IU/kg | 0.6 IU/kg |
| HbA1 | 13.2% | 7.2% |
| 24 h. albuminuria | 275 mg | 60 mg |

Thus, the inventive treatment is effective in diabetes mellitus.

Example 7

Atherosclerosis is a systemic disease that is accompanied by formation of specific atherosclerotic plaques in large and middle sized artery walls. Depends on the localization, stage and size of atherosclerotic plaques the disease has different clinical signs (angina, stroke and so on). The signs especially associated with organ dysfunction caused by systemic atherosclerosis are cured by drug therapy or by surgical operation. There is no cure for Atherosclerosis by drug therapy methods as for any systemic disease. An established method of prevention that delays the disease progression is therapy with inhibitors of 3 3-hydroxy-3-methylglutaryl-CoA (HMG CoA) reductase (Lovastatin, Parvastatine e.t.c.) leading to the inhibition of endogenous cholesterol synthesis and increasing of clearance of low density lipoproteins of blood plasma and it attenuates atherosclerosis development (New Concepts and Paradigms in Cardiovascular Medicine: The Noninvasive Management of Coronary Artery Disease, K. Lance Gould, THE AMERICAN JOURNAL OF MEDICINE, Volume 104, Jun. 22, 1998, 2s-17s). Disadvantages of such treatment are adverse effects (A safety look at currently available statins, Moghadasian M H, Expert Opin Drug Saf 2002 Sep. 1 pp. 269-74) and limited efficacy (Statins: balancing benefits, efficacy and safety, Clearfield M B, Expert Opin Pharmacother, 2002, May 3 pp. 469-77).

Influence of DNase Therapy on the Viability of Pancreatic Beta-Cells and Endothelium of Aorta Human recombinant DNase I (Gentech) was used. β cells of human embryonic pancreas and endothelial cells of human aorta were used for primary cell culture formation. DNA isolated from plasma of patient with severe form of diabetes mellitus type 2 that was complicated by atherosclerosis (0.0025 mkg on 1 ml of culture media) was added to one of the experimental series in cell culture 24 hours after passage and DNA extracted from the blood of the same patient but treated by DNase (1 mkg/ml; 37 C; 30 minutes) was added to the second series of cell culture. The number of viable cells was counted using the trypan blue uptake technique in a 24 hours.

Results of the experiment are presented in table 4:

TABLE 4

Percentage of viable cells 48 hours after their cultivation (in percents).

| Cells | Control | DNA of patient | DNA of patent treated by DNse |
|---|---|---|---|
| β cells | 73% | 43% | 61% |
| Endotelium | 62% | 35% | 55% |

Thus extracellular blood plasma DNA of patient with severe form of diabetes mellitus type 2 and atherosclerosis negatively influence both the normal pancreatic β-cells and the normal endothelial cells. Destruction of the patient' blood extracellular DNA prevents development of negative influence according to the claimed method.

Example 8. Treatment of the Generalized Infection (Sepsis)

38-years-old man has been admitted to the Department of Internal Medicine in grave condition. 12 days before acute respiratory syndrome was diagnosed him. Because of sub febrile temperature, asthenic syndrome and pain in the right chest half, pneumonia was diagnosed 5 days before hospitalization. Cefazoline injection and Roxitomicine per os were prescribed, but no improvement was observed, and two day before admittance to the hospital, fever (39.5-40° C.), sickness, headache were developed. Numerous hemorrhagic rush on the skin, muscle pain, jaundice and diarrhea appeared in the last day before hospitalization. To the time of admittance to the hospital, temperature was 38.3 C, arterial pressure was 100/60; tachycardia of 120 beats per minute, negative meningeal symptoms, cold and cyanotic limbs were found out. Data of laboratory examination: moderate leucocytosis and left shift of hemogram (18% of young forms) was present, appearance of neutrophils with toxic granulation, increasing of conjugated bilirubin, AST and ALT. Numerous small zones of heterogeneity were found at liver' ultrasound examination. The patient was diagnosed as having sepsis. Bacteriological control of blood was done. Gentamicin/Ampicillin/Metronidazole, heparin, vasodilators were per-orally used for treatment. In spite of antimicrobial polychemotherapy, hemabsorption and blood plasma transfusion patient' condition has become worse. Vancomycin' infusions were prescribed as *S. pneumonia* was isolated from the patient' blood. During next 48 hours in spite of Vancomycin's infusions condition of patient continued to become worse. Symptoms of multiple organ failure have appeared. Intravenous non-stop infusions of bovine pancreatic DNase at 800 mg/day (1 600 000 Kunitz units) dose were started after parents' approbation. Symptoms of condition' stabilization have appeared twelve hours after initiation of DNase infusion. They were: improvement of peripheral blood circulation and indexes of systemic haemodynamic, appearance of urination. DNase' infusions continued during next 5 days. At that time patient laboratory indexes, haemodynamic, renal function become normal and patient was transferred on self-dependent breathing.

Thus DNase' use according to the claimed method possess therapeutic effect at systemic bacterial infection.

INDUSTRIAL APPLICABILITY

For the realization the methods there were used well-known materials and equipment manufactured in plant conditions and according to aforesaid the invention conformances to requirements of "industrial applicability" criteria (IA).

What is claimed is:

1. A method for normalization of kidney function in a subject suffering from diabetes, said method comprising administering to said subject a DNase enzyme, wherein said DNase enzyme is administered in a dose and regimen which is sufficient to decrease the average molecular weight of extracellular blood DNA in the blood of said subject.

2. The method according to claim 1, wherein said DNase enzyme is administered in a dose and regimen that results in a DNA hydrolytic activity measured in blood plasma that exceeds 1.5 Kunitz units per 1 ml of blood plasma for more than 12 hours within a period of 24 hours.

3. A method for normalization of kidney function in a subject suffering from a systemic infection, said method comprising administering to said subject a DNase enzyme, wherein said DNase enzyme is administered in a dose and regimen which is sufficient to decrease the average molecular weight of extracellular blood DNA in the blood of said subject.

4. The method according to claim 3, wherein said DNase enzyme is administered in a dose and regimen that results in a DNA hydrolytic activity measured in blood plasma that exceeds 1.5 Kunitz units per 1 ml of blood plasma for more than 12 hours within a period of 24 hours.

5. The method according to claim 3, wherein said systemic infection is sepsis.

* * * * *